(12) United States Patent
Hosac

(10) Patent No.: US 10,980,296 B1
(45) Date of Patent: Apr. 20, 2021

(54) FACEMASK SUSTENANCE ACCESS PORT ASSEMBLY

(71) Applicant: Tracy Hosac, Pittsburgh, PA (US)

(72) Inventor: Tracy Hosac, Pittsburgh, PA (US)

( * ) Notice: Subject to any disclaimer, the term of this patent is extended or adjusted under 35 U.S.C. 154(b) by 0 days.

(21) Appl. No.: 16/899,625

(22) Filed: Jun. 12, 2020

(51) Int. Cl.
| | | |
|---|---|---|
| *A41D 13/11* | (2006.01) | |
| *A62B 18/10* | (2006.01) | |
| *A62B 9/00* | (2006.01) | |
| *A62B 18/02* | (2006.01) | |
| *A61M 15/00* | (2006.01) | |

(52) U.S. Cl.
CPC ............ *A41D 13/11* (2013.01); *A62B 9/00* (2013.01); *A62B 18/10* (2013.01); *A41D 2400/46* (2013.01); *A61M 15/0026* (2014.02); *A62B 18/025* (2013.01)

(58) Field of Classification Search
CPC .......................... A41D 13/11; A41D 2400/46; A41D 13/1218; A61M 1/0058; A61M 15/00; A61M 15/0026; A61M 16/0427; A61M 16/0488; A61M 16/0497; A61M 16/20; A61M 16/208; A61M 39/20; A61M 39/26; A61M 2039/2426; A61F 9/06; F41H 1/04; Y10S 128/912
USPC ............ 128/202.15, 205.27, 206.12, 206.19
See application file for complete search history.

(56) References Cited

U.S. PATENT DOCUMENTS

| | | | | | |
|---|---|---|---|---|---|
| 2,023,267 | A | * | 12/1935 | Saint Rapt ........... | A62B 18/086 128/202.15 |
| 4,823,785 | A | * | 4/1989 | Mancosu .............. | A62B 18/086 128/202.15 |
| 4,841,963 | A | * | 6/1989 | Vandeputte .......... | A62B 18/086 128/202.15 |
| 4,890,609 | A | * | 1/1990 | Wilson, II ............. | A61M 16/06 128/206.28 |
| 4,971,048 | A | | 11/1990 | Seekins | |
| 5,080,094 | A | * | 1/1992 | Tayebi ................. | A62B 23/025 128/205.29 |
| 6,325,116 | B1 | * | 12/2001 | Savage ................ | A62B 18/086 128/206.22 |
| 6,615,829 | B2 | * | 9/2003 | Horn .................... | A62B 18/086 128/201.26 |
| 7,810,493 | B2 | | 10/2010 | Resnick | |
| 7,955,418 | B2 | * | 6/2011 | Claussen ........... | A61M 16/1065 95/135 |

(Continued)

*Primary Examiner* — Tu A Vo
*Assistant Examiner* — Alexander Morales
(74) *Attorney, Agent, or Firm* — Thomas M. Joseph, Esq.

(57) ABSTRACT

A flat mounting plate frictionally engages a protective facemask body inner surface, surrounds a first opening, at least partially, and defines a second opening that is co-extensive with the first opening, at least partially. A flat retaining plate frictionally engages the protective facemask body outer surface, surrounds the first opening, at least partially, and defines a third opening that is co-extensive with the first opening, at least partially. A tubular spacer is positioned between the flat mounting plate and the flat retaining plate inserted into the first opening to define a passageway connecting the second opening to the third opening for nourishment to flow therethrough. A gasket is positioned between the flat mounting plate and the flat retaining plate to seal the passageway. The flat mounting plate and the flat retaining plate define jaws for gripping the protective facemask body to hold the port assembly in place.

18 Claims, 5 Drawing Sheets

(56) References Cited

U.S. PATENT DOCUMENTS

| | | | |
|---|---|---|---|
| 7,958,889 B1* | 6/2011 | Fernandez-Decastro | A62B 18/086 |
| | | | 128/202.15 |
| 10,478,667 B2* | 11/2019 | Tao | A63B 21/00058 |
| 10,905,905 B1* | 2/2021 | Dettore | A62B 18/025 |
| 2005/0051235 A1* | 3/2005 | Kline | A62B 18/086 |
| | | | 141/351 |
| 2005/0284480 A1* | 12/2005 | Rittner | B64D 11/00 |
| | | | 128/205.25 |
| 2006/0090754 A1* | 5/2006 | Mittelstadt | A62B 23/02 |
| | | | 128/201.17 |
| 2007/0156118 A1* | 7/2007 | Ramsey | A61M 39/20 |
| | | | 604/533 |
| 2012/0103327 A1* | 5/2012 | Low | A62B 18/086 |
| | | | 128/202.15 |
| 2013/0032153 A1* | 2/2013 | Neely | A61M 16/06 |
| | | | 128/205.25 |
| 2016/0074683 A1* | 3/2016 | Bergeron | A62B 18/08 |
| | | | 128/201.19 |
| 2016/0263337 A1* | 9/2016 | Borsari | A61M 16/0616 |
| 2017/0035136 A1* | 2/2017 | van Heerden | B63C 11/02 |
| 2017/0209656 A1* | 7/2017 | Linton | A61M 16/0841 |
| 2018/0280758 A1* | 10/2018 | Tao | A63B 21/00058 |

\* cited by examiner

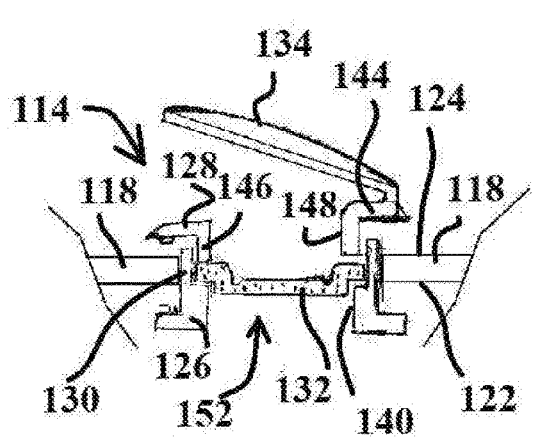
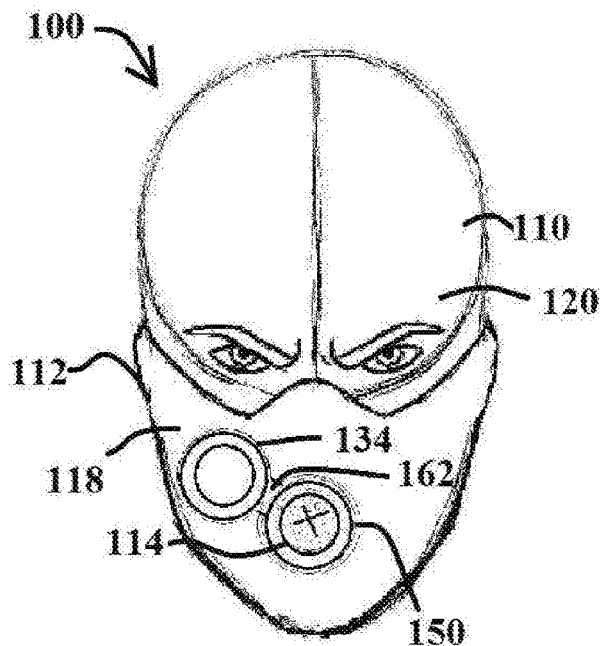
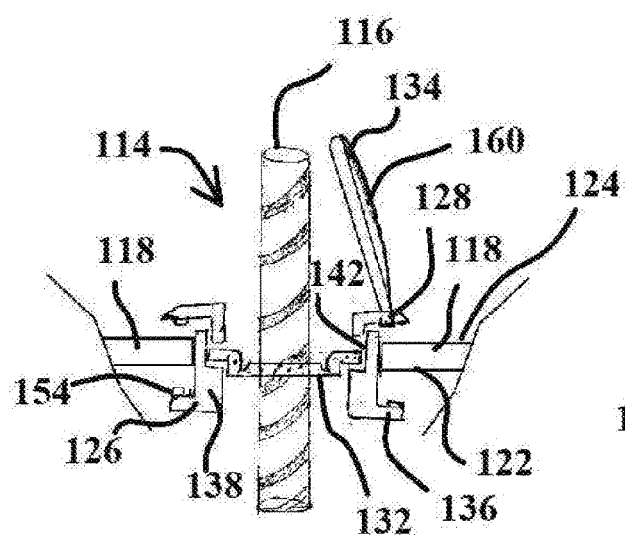
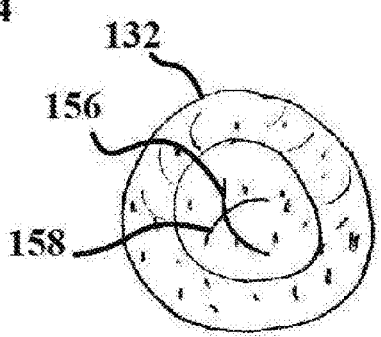
FIG. 1
FIG. 2
FIG. 3
FIG. 4

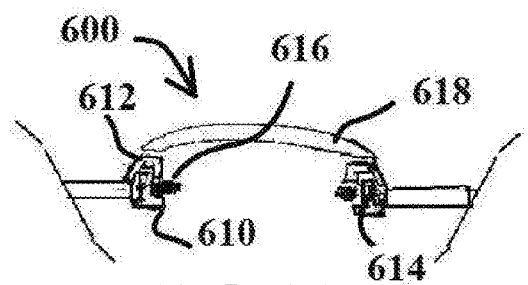
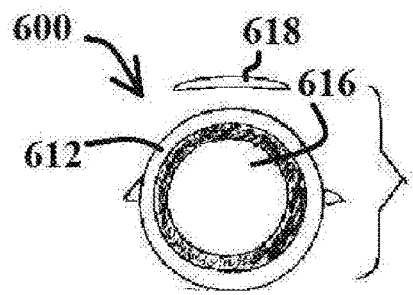
FIG. 15
FIG. 16
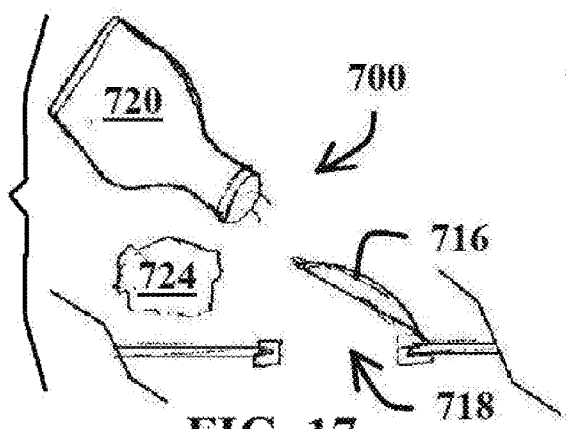
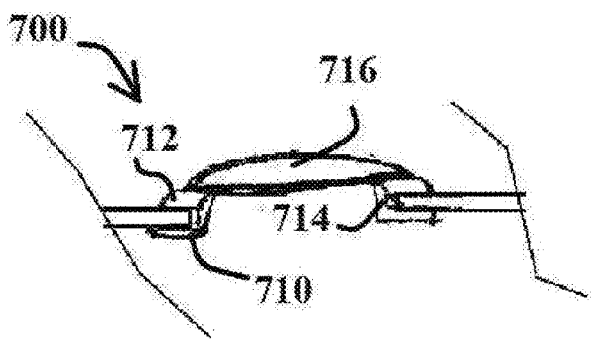
FIG. 17
FIG. 18
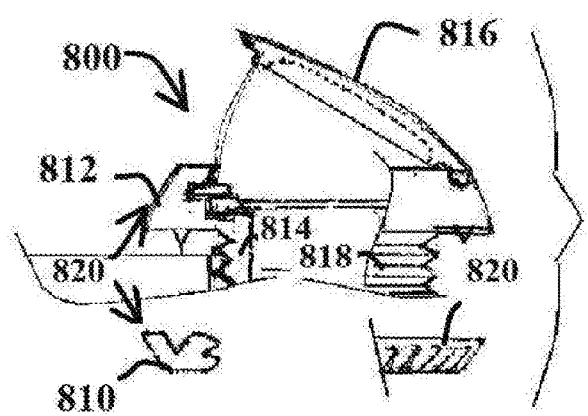
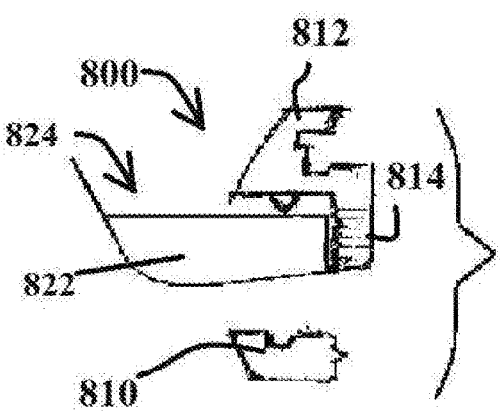
FIG. 19
FIG. 20

FACEMASK SUSTENANCE ACCESS PORT ASSEMBLY

BACKGROUND

The air quality in many everyday situations in heavily populated areas can be very poor. In larger cities, the heavy density of cars, buses, trucks and motorcycles often emit excessive amounts of toxic pollutants. Power plants are another key source of pollutions. Natural or man-made disasters, such as sandstorms, fires of any kinds, also contribute harm to the respiratory systems of the general population. Additionally, SARS, bird influenza, swine influenza, and COVID-19, which are four of the most recent, deadly air borne infectious agents, represent air borne threats to humans.

One potential way to address problems with air quality is to use facemasks. Facemasks can maintain a private, enclosed space around the breathing orifices when a person is in close proximity to other persons, or if an undesirable atmospheric agent is present. Additionally, infectious persons can wear masks to protect other people in the vicinity from their pathogens.

Facemasks have become ubiquitous during the on-going COVID-19 crisis. These protective face covers can be designed to minimize the transmission of contagious diseases or to protect the respiratory system from toxic substances or allergens in the surrounding atmosphere.

Different variations of facemasks have different features, such as different ways of retaining the mask in place, providing different degrees of comfort for the wearer. However, facemasks and other respiratory protective devices are only effective when such devices are worn properly.

Once a wearer takes off a mask, even partially, the wearer risks environmental exposure. Wearers that get hot, thirsty and/or hungry cannot relieve these conditions while wearing a facemask. Currently, wearers must remove the facemask and risk exposure to possible hazardous conditions. As a result, some masks and/or respiratory systems have been designs to allow wearers to alleviate these conditions.

One type of military respirator system includes a drinking tube with an external fluid supply. However, the drinking tube is in a fixed position. In other embodiments, the drinking tube can be mounted inside the mask with a retractable drink system that is cumbersome and awkward to use. Accordingly, there is a need for an improved respiratory protective device that allows a person to get sustenance and still enjoy protection in a hazardous environment.

SUMMARY

The following summary is provided to introduce a selection of concepts in a simplified form that are further described below in the detailed description. This summary is not intended to identify key features or essential features of the claimed subject matter, nor is it intended to be used to limit the scope of the claimed subject matter.

In various implementations, a port assembly provides access to a first opening in a protective facemask that includes a body for covering at least a portion of the face of a wearer that includes the mouth with the body having an inner surface adjacent to the face and an outer surface on the opposite side thereof. An essentially flat mounting plate frictionally engages the protective facemask body inner surface, surrounds the first opening, at least partially, and defines a second opening that is co-extensive with the first opening, at least partially. An essentially flat retaining plate frictionally engages the protective facemask body outer surface, surrounds the first opening, at least partially, and defines a third opening that is co-extensive with the first opening, at least partially. A tubular spacer is positioned between the essentially flat mounting plate and the essentially flat retaining plate inserting into the first opening to define a passageway connecting the second opening to the third opening for nourishment to flow therethrough. A gasket is positioned between the essentially flat mounting plate and the essentially flat retaining plate to seal the passageway. The essentially flat mounting plate and the essentially flat retaining plate define jaws for gripping the protective facemask body to hold the port assembly in place.

In other implementations, an apparatus for providing access to a first opening in a protective facemask that includes a body for covering at least a portion of the face of a wearer that includes the mouth with the body having an inner surface adjacent to the face and an outer surface on the opposite side thereof. A valve assembly has a mounting plate adjacent to the facemask body inner surface, a retaining plate adjacent to the facemask body outer surface, and a spacer positioned between the mounting plate and the retaining plate. The valve assembly has gripping means for connecting to the valve body. The valve assembly has a bore extending through the mounting plate, the retaining plate, and the spacer to define a passageway for receiving nourishment therethrough. A gasket or a lid seals the passageway.

In yet other implementations, a system protects the respiratory system of a wearer. A protective facemask has a body for covering at least a portion of the face of the wearer that includes the mouth with the body having an inner surface adjacent to the face and an outer surface on the opposite side thereof. A valve assembly has a mounting plate adjacent to the facemask body inner surface, a retaining plate adjacent to the facemask body outer surface, a spacer positioned between the mounting plate and the retaining plate, and a gasket. A tubular nourishment delivery device is provided. The mounting plate and retaining plate define a connector to connect the valve assembly to the protective facemask. The valve assembly and the protective facemask have a bore extending through the mounting plate, the retaining plate, and the spacer to define a passageway to mouth of the wearer with the tubular nourishment delivery device extending therethrough. The gasket surrounds the tubular nourishment delivery device, at least partially.

These and other features and advantages will be apparent from a reading of the following detailed description and a review of the appended drawings. It is to be understood that the foregoing summary, the following detailed description and the appended drawings are explanatory only and are not restrictive of various aspects as claimed.

BRIEF DESCRIPTION OF THE DRAWINGS

FIG. 1 is a perspective view of a system for protecting the respiratory system of a wearer in accordance with the disclosure.

FIG. 2 is a fragmentary view in side elevation of a valve assembly is accordance with the disclosure.

FIG. 3 is a fragmentary view in side elevation of the valve assembly shown in FIG. 2 with a nourishment delivery device inserted therein.

FIG. 4 is a top plan view of the valve assembly shown in FIG. 2.

FIG. 15 is a fragmentary view in side elevation of another embodiment of a valve assembly in accordance with the disclosure.

FIG. 16 is a top perspective view of the valve assembly shown in FIG. 15.

FIG. 17 is a fragmentary view in side elevation of another embodiment of a valve assembly in accordance with the disclosure.

FIG. 18 is a fragmentary view in side elevation of the valve assembly shown in FIG. 17.

FIG. 19 is an exploded, fragmentary view in side elevation of another embodiment of a valve assembly in accordance with the disclosure.

FIG. 20 is another exploded, fragmentary view in side elevation of the valve assembly shown in FIG. 19.

DETAILED DESCRIPTION

Figure 5:
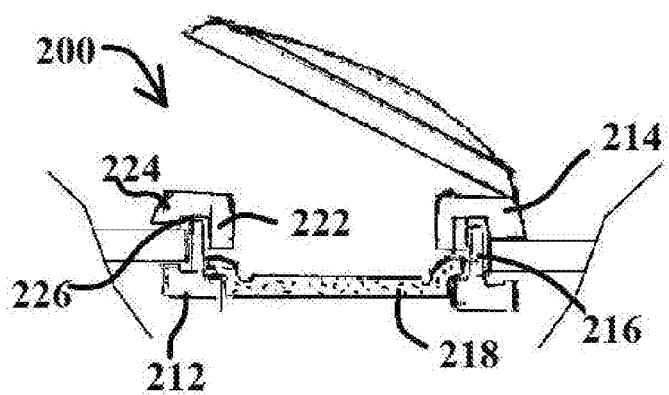
FIG. 5 is a fragmentary view in side elevation of another embodiment of a valve assembly in accordance with the disclosure.
Figure 6:
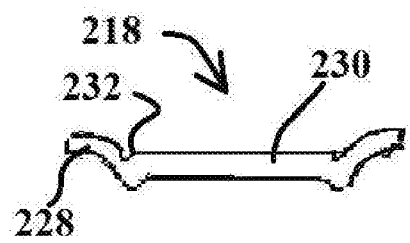
FIG. 6 is a view in side elevation of a gasket that can be used with the valve assembly shown in FIG. 5.
Figure 7:
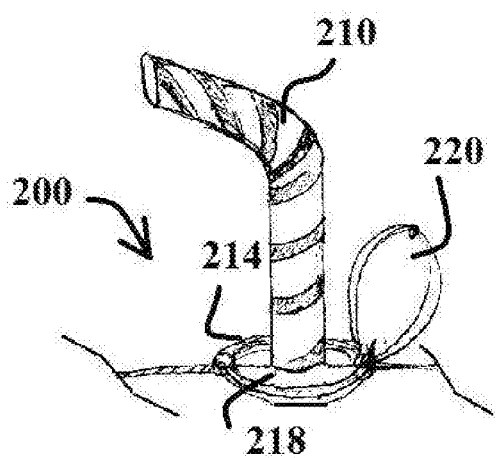
FIG. 7 is a fragmentary perspective view of the valve assembly shown in FIG. 5 with a nourishment delivery device inserted therein.
Figure 8:
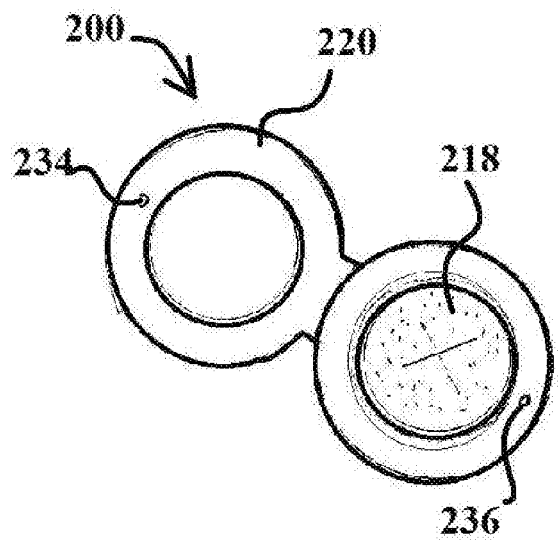
FIG. 8 is a top plan view of the valve assembly shown in FIG. 5.

The subject disclosure is directed to a respiratory protective device, facemask, or mask that can prevent the wearer from spreading COVID-19 and other airborne viruses while eating or drinking. The facemask can be adapted, particularly, to facilitate the delivery of sustenance while wearing a protective device. More specifically, the subject disclosure is directed to a system for delivering nourishment through a straw or other tubular delivery device to the mouth of a person through a mask. The mask includes a valve or port assembly that defines a passageway for receiving the straw. The device can be sold as a kit.

The detailed description provided below in connection with the appended drawings is intended as a description of examples and is not intended to represent the only forms in which the present examples can be constructed or utilized. The description sets forth functions of the examples and sequences of steps for constructing and operating the examples. However, the same or equivalent functions and sequences can be accomplished by different examples.

References to "one embodiment," "an embodiment," "an example embodiment," "one implementation," "an implementation," "one example," "an example" and the like, indicate that the described embodiment, implementation or example can include a particular feature, structure or characteristic, but every embodiment, implementation or example can not necessarily include the particular feature, structure or characteristic. Moreover, such phrases are not necessarily referring to the same embodiment, implementation or example. Further, when a particular feature, structure or characteristic is described in connection with an embodiment, implementation or example, it is to be appreciated that such feature, structure or characteristic can be implemented in connection with other embodiments, implementations or examples whether or not explicitly described.

Numerous specific details are set forth in order to provide a thorough understanding of one or more embodiments of the described subject matter. It is to be appreciated, however, that such embodiments can be practiced without these specific details.

Various features of the subject disclosure are now described in more detail with reference to the drawings, wherein like numerals generally refer to like or corresponding elements throughout. The drawings and detailed description are not intended to limit the claimed subject matter to the particular form described. Rather, the intention is to cover all modifications, equivalents and alternatives falling within the spirit and scope of the claimed subject matter.

The subject respiratory protective system includes a port assembly or a valve assembly that provides an opening by means of a molded three-dimensional structure that can be incorporated into a protective facemask. The molded structure sandwiches the mask materials to provide the opening for the user to receive nourishment through the mask. The wearer can receive nourishment via the port without introducing contamination from the external environment. The valve assembly or the port assembly can include a cover to keep airborne particles from penetrating the mask and a food-grade silicone barrier with an orifice designed to stretch and seal around a tubular nourishment delivery device.

In some embodiments, a facemask access port includes a molded three-dimensional structure that includes an upper body, a cover, and a retention fitting that has at least one orifice that allows access to the interior of the mask. The three dimensional structure can be molded out of thermoplastic in some instances. In other instances, the three-dimensional structure can be molded and manufactured out of other materials, such as metals, fiberglass and other materials.

The upper body that can be configured to fit together to form sandwiched structure through snapping, clipping, compression, gluing, screwing or other fastening methods. The sandwiched structure surround an inner edge of a hole in the mask materials, at least partially. In applications in which the molded three-dimensional structure has a hinge, snap or screw cover, the molded three-dimensional structure can seal against mask material and protect the orifice and internal structure from contamination.

In other embodiments, the molded three-dimensional structure includes an upper body and a retention fitting that has at least one orifice to allow access to the interior of the mask. The retention fitting can sandwich all layers together with the mask material forming a middle layer between the upper body and the retention fitting. The upper body, the retention fitting, and the mask material have a series of coextensive holes that form a passageway that is in fluid communication with the mouth of the wearer.

The structure can include a cover that attaches to the upper body via snap, clip, compression or hinges, and/or sandwiching a valve/gasket made of flexible silicone rubber or similar materials. The valve/gasket can have an orifice of cross cut or small hole for the introduction of liquid sustenance through a tubular nourishment deliver device, such as a straw. Alternatively, the orifice can include a large inlet to accommodate food or snacks, such as soda or candy.

Referring now to the drawings and, particularly, to FIGS. 1-4, there is shown a system, generally designated by the numeral 100, for protecting the respiratory system of a wearer 110. The system 100 includes a protective facemask 112, a port assembly or valve assembly 114, and a tubular nourishment delivery device 116. The system 100 is particularly adapted to protect the wearer 110 from various airborne hazards. Additionally, the system 100 is adapted to prevent the wearer 110 from spreading the COVID-19 virus while eating or drinking.

The COVID-19 virus is believed to be transmitted through airborne droplets that are exhaled from infected individuals. The facemask 112 should prevent such droplets from being spread, so that the system 100 can prevent the spread of the COVID-19 virus, as well as any other infectious agent that is transmitted through airborne droplets.

The tubular nourishment delivery device 116 has the ability to deliver nourishment through the facemask 112 and the valve assembly 114. In order to accomplish this function, the nourishment delivery device 116 can be inserted into facemask 112 through the valve assembly 114, so that it is in fluid communication with the mouth (not shown) of the wearer 110. As a result, the wearer 110 can receive nourishment from the tubular nourishment delivery device 116 while the facemask 112 continues to protect the wearer 110.

The protective facemask 112 has a body 118 for covering at least a portion of the face 120 of the wearer 110. The body 118 includes one or more layers of protective material that can be rigid, semi-rigid, or flexible. Additionally, the body 118 has an inner surface 122 adjacent to the face 120 and an outer surface 124 on the opposite side of the face 120.

The valve assembly 114 has a tubular mounting plate 126, a tubular retaining plate 128, a tubular spacer 130, a gasket 132, and a lid 134. The mounting plate 126 is adjacent to the inner surface 122. The retaining plate 128 is adjacent to the outer surface 124. The spacer 130 is positioned between the mounting plate 126 and the retaining plate 128.

The mounting plate 126 has an essentially flat, annular lower section 136 with a raised ledge 138 projecting upwardly therefrom to define an opening 140 therein to form a flange. The spacer 130 projects upwardly from the ledge 138 to define an opening 142 therein. In this exemplary embodiment, the spacer 130 forms a unitary structure with the mounting plate 126. In other embodiments, the mounting plate 126 and the spacer 130 can be integral, joined components, or separate components.

The retaining plate 128 has an essentially flat, annular upper section 144 with a raised ledge 146 projecting downwardly therefrom to define an opening 148 therein to form a flange. The openings 140, 142, 148 are aligned to one another and are co-extensive with an opening 150 in the facemask 112 to form a passageway 152 for receiving nourishment that can flow through the tubular nourishment delivery device 116. The mounting plate lower section 136 surrounds the opening 150, at least partially.

As shown in FIGS. 1-4, the mounting plate 126, the retaining plate 128, and the tubular spacer 130 form jaws for gripping the body 118 on one side to hold the valve assembly 114 in place on the facemask 112. The mounting plate 126, the retaining plate 128, and the tubular spacer 130 form jaws for gripping the gasket 132 on the opposite side.

The valve assembly 114 can include fastening devices 154 to enhance the frictional engagement with the body 118. In this exemplary embodiment, the fastening devices 154 are gripping surfaces or grips. In other embodiments, the fastening devices 154 can include screws, snaps, and clips.

The gasket 132 can seal the valve assembly 114 to prevent airborne contaminants from getting under the facemask 112 and to prevent wearer 110 from exhaling infectious agents via droplets. The gasket 132 is positioned between the mounting plate 126 and the retaining plate 128 to seal the passageway 152. In this exemplary embodiment, the gasket 132 includes a pair of crosscuts 156-158 to form an opening to receive the nourishment delivery device 116.

The gasket 132 can be made from a flexible material, such as food grade silicone. In other embodiments, the gasket 132 can be made from other suitable thermoplastics, thermoplastic elastomers, elastomers, plastomers, rubbers, network polymer materials, and plastic composite materials.

The lid 134 can cover the valve assembly 114 to prevent airborne contaminants from getting under the facemask 112 and to prevent wearer 110 from exhaling infectious agents via droplets. The lid 134 is an essentially round dome 160 that covers the passageway 152 with an extension 162 that connects to the retaining plate 128.

The lid 134 is pivotally attached to the retaining plate 128, so that it can be opened and closed to provide the nourishment delivery device 116 with access to the mount (not shown) of the wearer 110. The lid 134 can be permanently attached to the retaining plate 128 or releasably attached to the retaining plate 128. In some embodiments, the lid 134 can snap off from the retaining plate 128 with no additional means for connecting the lid 134 to the retaining plate 128.

The nourishment delivery device 116 can be any suitable device that supplies liquid sustenance to the wearer 110. In this exemplary embodiment, the nourishment delivery device 116 is a straw.

The mounting plate 126, the retaining plate 128, the tubular spacer 130, and the lid 134 can be made from any suitable material through any suitable manufacturing method. Suitable materials include flexible, rigid, or semi-rigid materials. Suitable materials include opaque materials, translucent materials, and transparent materials.

Suitable materials also include metals, ceramics, glasses, plastics, and composites. Such materials can include recyclable or recycled materials. In some embodiments, the suitable materials can include plastic materials, such as thermosets, thermoplastics, thermoplastic elastomers, elastomers, plastomers, rubbers, network polymer materials, and plastic composite materials. In this exemplary embodiment, the mounting plate 126, the retaining plate 128, the tubular spacer 130, and the lid 134 are made from molded plastics.

It should be understood that individual components of the above-described valve assembly 114 can be made of a material that is specifically suited for the individual structural tolerances. Any combination of material or a uniform application of a single material that results in an acceptably robust structure is suitable.

Referring now to FIGS. 5-8 with continuing reference to the foregoing figures, there is shown another embodiment of a port assembly or valve assembly, generally designated with the numeral 200. Like the embodiment shown in FIGS. 1-4, the valve assembly 200 is configured to interface with a nourishment delivery device 210 to provide nourishment to a wearer, such as the wearer 110 shown in FIGS. 1-4.

The valve assembly 200 has a tubular mounting plate 212, a tubular retaining plate 214, a tubular spacer 216, a gasket 218, and a lid 220. The valve assembly 200 is configured to snap, screw, or clip together to provide an easy fit.

Unlike the embodiment shown in FIGS. 1-4, the retaining plate 214 includes a pair of rims 222-224 that define a channel 226 therebetween. The spacer 216 projects upwardly from the mounting plate 212 to engage, frictionally, the gasket 218 and hold it in place.

The gasket 218 is an essentially flat annular disk with a circular lip 228 that is separate and distinct from a center section 230 by a groove 232. The groove 232 facilitates the bending of the lip 228 upwardly, at an angle from the center section 230. The lip 228 can be gripped by the rim 224 to hold the gasket 218 in place.

The lid 220 can include a projection 234. The projection 234 can be inserted into a notch 236 in the retaining plate 214 to facilitate the closing of the lid 220 against the retaining plate 214 to close the valve assembly 200.

Figure 9:
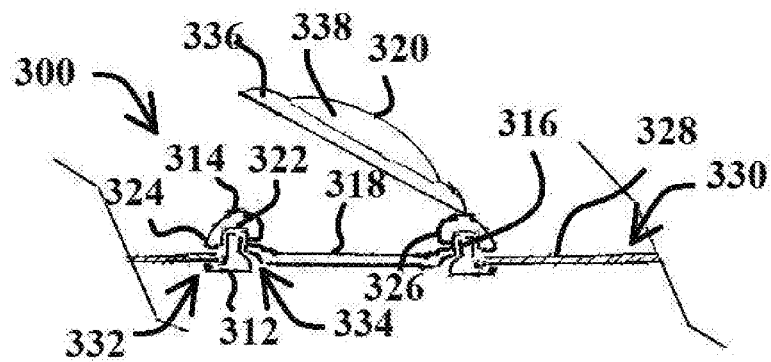
FIG. 9 is a fragmentary view in side elevation of another embodiment of a valve assembly in accordance with the disclosure.
Figure 10:
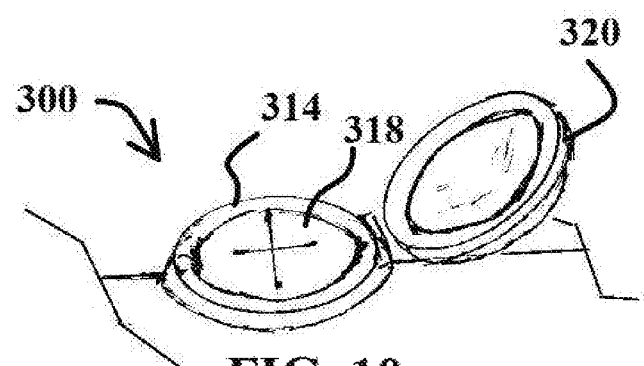
FIG. 10 is a fragmentary perspective view of the valve assembly shown in FIG. 8.
Figure 11:
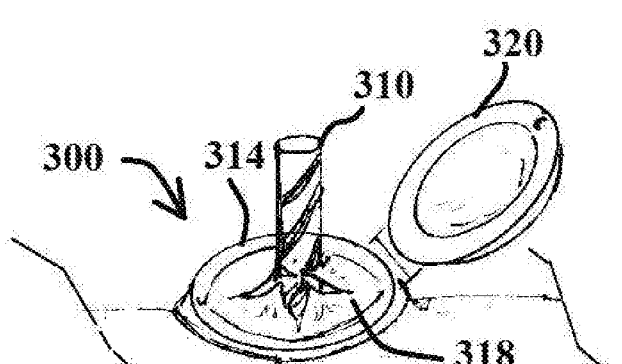
FIG. 11 is a fragmentary perspective view of the valve assembly shown in FIG. 9 with a nourishment delivery device inserted therein.

Referring now to FIGS. 9-11 with continuing reference to the foregoing figures, there is shown another embodiment of a port assembly or valve assembly, generally designated with the numeral 300. Like the embodiments shown in FIGS. 1-8, the valve assembly 300 is configured to interface with a nourishment delivery device 310 to provide nourishment to a wearer, such as the wearer 110 shown in FIGS. 1-4. The valve assembly 300 has a tubular mounting plate 312, a tubular retaining plate 314, a tubular spacer 316, a gasket 318, and a lid 320.

Unlike the embodiments shown in FIGS. 1-8, the retaining plate 314 includes a shallow groove 322 that separates the retaining plate 314 into an outer edge 324 and an inner edge 326. The spacer 316 projects upwardly from the mounting plate 312 into the groove 322. The spacer 316 has a thickness that is greater than the thickness of the body 328 of a facemask 330.

The mounting plate 312, the spacer 316, and the outer edge 324 form a jaw 332 to engage, frictionally, the facemask body 328. The mounting plate 312, the spacer 316, and the inner edge 326 form a jaw 334 to engage, frictionally, the gasket 318.

The lid 320 is pivotally connected to the retaining plate 314. The lid 320 includes an essentially cylindrical lower body 336 and a dome 338.

Figure 12:
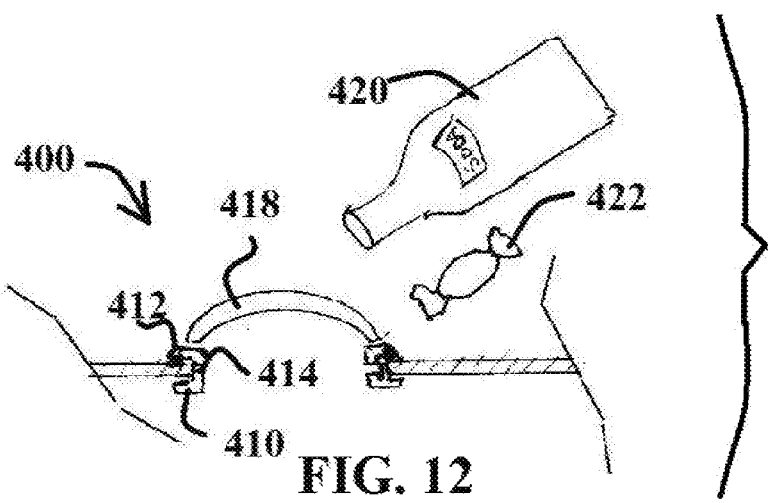
FIG. 12 is a fragmentary view in side elevation of another embodiment of a valve assembly in accordance with the disclosure.
Figure 13:
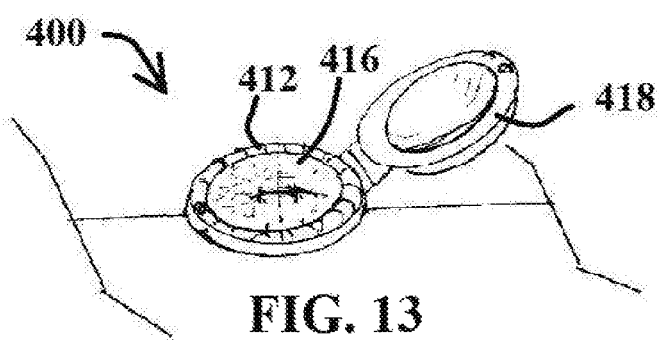
FIG. 13 is a fragmentary perspective view of the valve assembly shown in FIG. 12.

Referring now to FIGS. 12-13 with continuing reference to the foregoing figures, there is shown another embodiment of a port assembly or valve assembly, generally designated with the numeral 400. Like the embodiments shown in FIGS. 1-11, the valve assembly 400 has a tubular mounting plate 410, a tubular retaining plate 412, a tubular spacer 414, a gasket 416, and a lid 418.

Unlike the embodiments shown in FIGS. 1-11, the valve assembly 400 is configured to facilitate the delivery of nourishment through a pair of nourishment delivery devices 420-422. The nourishment delivery device 420 is a soda bottle. The nourishment delivery device 422 is a wrapped piece of candy. The gasket 416 includes an opening 424 that is sufficiently large to receive liquid from the nourishment delivery device 420 and/or food from the nourishment delivery device 422.

Figure 14:
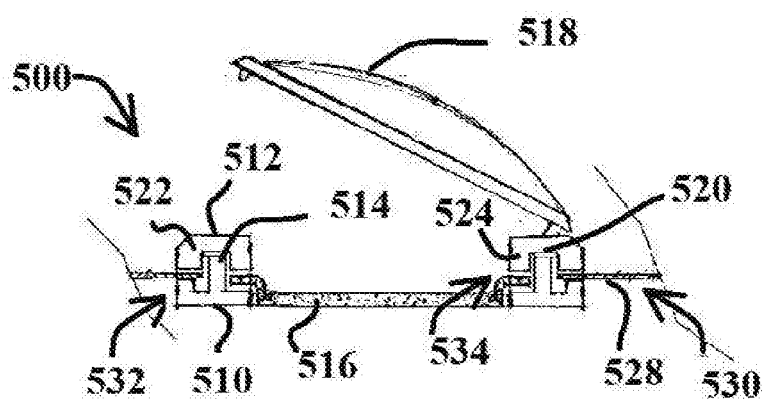
FIG. 14 is a fragmentary view in side elevation of another embodiment of a valve assembly in accordance with the disclosure.

Referring now to FIG. 14 with continuing reference to the foregoing figures, there is shown another embodiment of a port assembly or valve assembly, generally designated with the numeral 500. Like the embodiments shown in FIGS. 1-13, the valve assembly 500 has a tubular mounting plate 510, a tubular retaining plate 512, a tubular spacer 514, a gasket 516, and a lid 518.

The retaining plate 512 includes a shallow groove 520 that separates the retaining plate 512 into an outer edge 522 and an inner edge 524. The spacer 514 projects upwardly from the mounting plate 510 into the groove 520. Unlike the embodiments shown in FIGS. 1-13, the mounting plate 510 includes a raised rim 526 to facilitate the gripping of a body 528 for a facemask 530.

The raised rim 526 and the outer edge 522 form a jaw 532 to engage, frictionally, the facemask body 528. The mounting plate 510, the spacer 514, and the inner edge 524 form a jaw 534 to engage, frictionally, the gasket 516.

Referring now to FIGS. 15-16 with continuing reference to the foregoing figures, there is shown another embodiment of a port assembly or valve assembly, generally designated with the numeral 600. Like the embodiments shown in FIGS. 1-14, the valve assembly 600 has a tubular mounting plate 610, a tubular retaining plate 612, a tubular spacer 614, a gasket 616, and a lid 618.

Unlike the embodiments shown in FIGS. 1-14, the gasket 616 does not include an elongated opening. Rather, the gasket 616 forms a membrane that can be punctured with a syringe or needle (not shown). The use of a sealed membrane is particularly useful in applications involving hazmat suits, personal protective equipment, and sanitary clothing worn by surgeons, nurses, physicians and other workers involved in patient care in hospitals.

Referring now to FIGS. 17-18 with continuing reference to the foregoing figures, there is shown another embodiment of a port assembly or valve assembly, generally designated with the numeral 700. Like the embodiments shown in FIGS. 1-16, the valve assembly 700 has a tubular mounting plate 710, a tubular retaining plate 712, a tubular spacer 714 and a lid 716. The lid 716 can be pivotally attached to the retaining plate 712. The lid 716 can be moved from an open position to a closed position to seal a passageway 718 in the valve assembly 700.

Unlike the embodiments shown in FIGS. 1-16, the valve assembly 700 does not include a gasket, such as the gasket 132 shown in FIGS. 1-4, the gasket 218 shown in FIGS. 5-8, the gasket 318 shown in FIGS. 9-11, the gasket 416 shown in FIGS. 12-13, the gasket 516 shown in FIG. 14, and/or the gasket 616 shown in FIGS. 15-16. Rather, the mounting plate 710, the retaining plate 712, and the tubular spacer 714 define a passage way 718 that is sufficiently large to receive liquid from the nourishment delivery device 720 and/or to accommodate food from the nourishment delivery device 722.

Referring now to FIGS. 19-20 with continuing reference to the foregoing figures, there is shown another embodiment of a port assembly or valve assembly, generally designated with the numeral 800. Like the embodiments shown in FIGS. 1-18, the valve assembly 800 has a tubular mounting plate 810, a tubular retaining plate 812, a tubular spacer 814 and a lid 816. The lid 816 can be pivotally attached to the retaining plate 812.

Unlike the embodiments shown in FIGS. 1-18, the spacer 814 extends downwardly from the retaining plate 812. The spacer 814 includes a threaded surface 818 that can mate with a threaded surface 820 on the mounting plate 810.

The spacer threaded surface 818 can connect to the mounting plate threaded surface 820 to releasably connect the mounting plate 810 to the retaining plate 812. The mounting plate 810, the retaining plate 812, and the spacer 814 form jaws 820 that grip a body 822 to connect the valve assembly 800 to a facemask 824.

Supported Features and Embodiments

The detailed description provided above in connection with the appended drawings explicitly describes and supports various features of a facemask sustenance access port assembly. By way of illustration and not limitation, supported embodiments include a port assembly for providing access to a first opening in a protective facemask, wherein the protective facemask includes a body for covering at least a portion of the face of a wearer that includes the mouth with the body having an inner surface adjacent to the face and an outer surface on the opposite side thereof, the port assembly comprising: an essentially flat mounting plate frictionally engaging the protective facemask body inner surface, surrounding the first opening, at least partially, and defining a second opening that is co-extensive with the first opening, at least partially, an essentially flat retaining plate frictionally engaging the protective facemask body outer surface, surrounding the first opening, at least partially, and defining a third opening that is co-extensive with the first opening, at least partially, a tubular spacer positioned between the essentially flat mounting plate and the essentially flat retaining plate inserting into the first opening to define a passageway connecting the second opening to the third opening for nourishment to flow therethrough, and a gasket positioned between the essentially flat mounting plate and the essentially flat retaining plate for sealing the passageway, wherein the essentially flat mounting plate and the essentially flat retaining plate define jaws for gripping the protective facemask body to hold the port assembly in place.

Supported embodiments include the foregoing port assembly, further comprising a removeable lid for covering the passageway.

Supported embodiments include any of the foregoing port assemblies, wherein the removeable lid is pivotally attached to the essentially flat retaining plate.

Supported embodiments include any of the foregoing port assemblies, wherein the first opening is essentially circular and the essentially flat retaining plate, the essentially flat mounting plate, and the tubular spacer define an annular ring for surrounding the first opening with the passageway extending therethrough.

Supported embodiments include any of the foregoing port assemblies, wherein the gasket is flexible.

Supported embodiments include any of the foregoing port assemblies, wherein the tubular spacer and the essentially flat mounting plate are unitary.

Supported embodiments include any of the foregoing port assemblies, wherein the gasket includes a fourth opening therein.

Supported embodiments include any of the foregoing port assemblies, wherein the jaws are connected to one another with fastening devices.

Supported embodiments include any of the foregoing port assemblies, wherein the fastening devices are selected from the group consisting of screws, snaps, and clips.

Supported embodiments include any of the foregoing port assemblies, wherein the spacer has a thickness that is greater than the thickness of the facemask body Supported embodiments include a system, a method, an apparatus, a kit, and/or means for implementing any of the foregoing port assemblies or a portion thereof.

Supported embodiments include an apparatus for providing access to a first opening in a protective facemask, wherein the protective facemask includes a body for covering at least a portion of the face of a wearer that includes the mouth with the body having an inner surface adjacent to the face and an outer surface on the opposite side thereof, the valve assembly comprising: a valve assembly having a mounting plate adjacent to the facemask body inner surface, a retaining plate adjacent to the facemask body outer surface, and a spacer positioned between the mounting plate and the retaining plate, the valve assembly having gripping means for connecting to the valve body, the valve assembly having a bore extending through the mounting plate, the retaining plate, and the spacer to define a passageway for receiving nourishment therethrough, and means for sealing the passageway.

Supported embodiments include the foregoing apparatus, further comprising a removeable cap for covering the passageway.

Supported embodiments include any of the foregoing apparatuses, wherein the removeable cap is pivotally attached to the retaining plate.

Supported embodiments include any of the foregoing apparatuses, wherein the spacer and the mounting plate are integral.

Supported embodiments include any of the foregoing apparatuses, wherein the spacer and the mounting plate are unitary.

Supported embodiments include any of the foregoing apparatuses, wherein the first opening is essentially circular and the valve assembly defines an annular ring for surrounding the first opening with the passageway extending therethrough.

Supported embodiments include any of the foregoing apparatuses, wherein the gasket is flexible.

Supported embodiments include any of the foregoing apparatuses, wherein the tubular spacer and the mounting plate are unitary.

Supported embodiments include any of the foregoing apparatuses, wherein the gasket includes a fourth opening therein.

Supported embodiments include any of the foregoing apparatuses, wherein the gripping means include fastening devices to connect the valve assembly to the facemask body.

Supported embodiments include any of the foregoing apparatuses, wherein the fastening devices are selected from the group consisting of screws, snaps, and clips.

Supported embodiments include an apparatus for providing access to a first opening in a protective facemask, wherein the protective facemask includes a body for covering at least a portion of the face of a wearer that includes the mouth with the body having an inner surface adjacent to the face and an outer surface on the opposite side thereof, the valve assembly comprising: a valve assembly having a mounting plate adjacent to the facemask body inner surface, a retaining plate adjacent to the facemask body outer surface, and a spacer positioned between the mounting plate and the retaining plate, the valve assembly having a bore extending through the mounting plate, the retaining plate, and the spacer to define a passageway for receiving nourishment therethrough, means for connecting the valve assembly to the valve body, and means for sealing the passageway.

Supported embodiments include a system, a method, a kit, and/or means for implementing any of the foregoing apparatuses or a portion thereof.

Supported embodiments include a system for protecting the respiratory system of a wearer comprising: a protective facemask having a body for covering at least a portion of the face of the wearer that includes the mouth with the body having an inner surface adjacent to the face and an outer surface on the opposite side thereof, a valve assembly having a mounting plate adjacent to the facemask body inner surface, a retaining plate adjacent to the facemask body outer surface, a spacer positioned between the mounting plate and the retaining plate, and a gasket, and a tubular nourishment delivery device, wherein the mounting plate and retaining plate define a connector to connect the valve assembly to the protective facemask, wherein the valve assembly and the protective facemask have a bore extending through the mounting plate, the retaining plate, and the spacer to define a passageway to mouth of the wearer with the tubular nourishment delivery device extending therethrough, and wherein the gasket surrounds the tubular nourishment delivery device, at least partially.

Supported embodiments include the foregoing system, wherein the tubular nourishment delivery device is a device selected from the group consisting of a straw and a syringe.

Supported embodiments include any of the foregoing systems, further comprising a removeable cap for covering the passageway.

Supported embodiments include any of the foregoing systems, wherein the removeable cap is pivotally attached to the retaining plate.

Supported embodiments include any of the foregoing systems, wherein the facemask prevents the wearer from spreading the COVID-19 virus.

Supported embodiments include an apparatus, a method, a kit, and/or means for implementing any of the foregoing systems or a portion thereof.

Supported embodiments can provide various attendant and/or technical advantages in terms of a facemask that can be utilized to prevent exposure to and transmission of infectious diseases Supported embodiments include a facemask assembly that protects the wearer from various airborne hazards.

Supported embodiments include a facemask assembly that can prevent the wearer from spreading the COVID-19 virus while eating or drinking.

The detailed description provided above in connection with the appended drawings is intended as a description of examples and is not intended to represent the only forms in which the present examples can be constructed or utilized. It is to be understood that the configurations and/or approaches described herein are exemplary in nature, and that the described embodiments, implementations and/or examples are not to be considered in a limiting sense, because numerous variations are possible.

The specific processes or methods described herein can represent one or more of any number of processing strategies. As such, various operations illustrated and/or described can be performed in the sequence illustrated and/or described, in other sequences, in parallel, or omitted. Likewise, the order of the above-described processes can be changed.

Although the subject matter has been described in language specific to structural features and/or methodological acts, it is to be understood that the subject matter defined in the appended claims is not necessarily limited to the specific features or acts described above. Rather, the specific features and acts described above are presented as example forms of implementing the claims.

What is claimed is:

1. A port assembly for providing access to a mouth opening in a protective facemask,
   wherein the protective facemask includes a body for covering at least a portion of a face of a wearer, wherein the body has an inner surface adjacent to the face and an outer surface on an opposite side thereof, wherein the body of the facemask has the mouth opening directly in front of a mouth of the wearer, the port assembly comprising:
   a mounting plate frictionally engaging the protective facemask body inner surface, surrounding the mouth opening, at least partially, and defining a first opening that is co-extensive with the mouth opening, at least partially,
   a retaining plate frictionally engaging and directly contacting the protective facemask body outer surface, surrounding the mouth opening, at least partially, and defining a second opening that is co-extensive with the mouth opening, at least partially,
   a tubular spacer positioned between the mounting plate and the retaining plate inserted into the mouth opening to define a passageway connecting the first opening to the second opening for nourishment to flow therethrough, wherein the tubular spacer is unitary with the mounting plate,
   a gasket for sealing the passageway, wherein the gasket is frictionally engaged by and directly contacting the mounting plate and the retaining plate, and
   a removeable lid for covering the retaining plate, wherein the removable lid is unitary with the retaining plate,
   wherein the mounting plate and the retaining plate define jaws for gripping the protective facemask body to hold the port assembly in place, wherein the port assembly has a bore extending through the mounting plate, the retaining plate, and the spacer to define a passageway for passing a nourishment delivery device into the facemask through the port assembly so that the nourishment delivery device enters the mouth of the wearer.

2. The port assembly of claim 1, wherein the mounting plate and the retaining plate snap together.

3. The port assembly of claim 1, wherein the mouth opening is circular and the retaining plate, the mounting plate, and the tubular spacer define an annular ring for surrounding the mouth opening with the passageway extending therethrough.

4. The port assembly of claim 1, wherein the gasket includes a third opening therein.

5. The port assembly of claim 1, wherein the jaws are connected to one another with fastening devices.

6. The port assembly of claim 5, wherein the fastening devices are selected from the group consisting of screws, snaps, and clips.

7. The port assembly of claim 1, wherein the tubular spacer has a thickness that is greater than a thickness of the facemask body.

8. An apparatus for providing access to a mouth opening in a protective facemask,
   wherein the protective facemask includes a body for covering at least a portion of a face of a wearer, wherein the body has an inner surface adjacent to the face and an outer surface on an opposite side thereof, wherein the body of the facemask has the mouth opening directly in front of a mouth of the wearer, the apparatus comprising a valve assembly, the valve assembly comprising:
   a mounting plate frictionally engaging the protective facemask body inner surface, surrounding the mouth opening, at least partially, and defining a first opening that is co-extensive with the mouth opening, at least partially,
   a retaining plate frictionally engaging and directly contacting the protective facemask body outer surface, surrounding the mouth opening, at least partially, and defining a second opening that is co-extensive with the mouth opening, at least partially,
   a tubular spacer positioned between the mounting plate and the retaining plate inserted into the mouth opening to define a passageway connecting the first opening to the second opening for nourishment to flow therethrough, wherein the tubular spacer is unitary with the mounting plate, a gasket for sealing the passageway, wherein the gasket is frictionally engaged by and directly contacting the mounting plate and the retaining plate, and a removeable cap for covering the retaining plate, wherein the removable lid is unitary with the retaining plate, wherein the mounting plate and the retaining plate define jaws for gripping the protective facemask body to hold the valve assembly in place, wherein the valve assembly has a bore extending through the mounting plate, the retaining plate, and the spacer to define a passageway for passing a nourishment delivery device into the facemask through the valve assembly so that the nourishment delivery device enters the mouth of the wearer.

9. The apparatus of claim 8, wherein the removeable cap is made from rigid molded plastic and the gasket is made from flexible plastic.

10. The apparatus of claim 8, wherein the mounting plate and the retaining plate snap together with the spacer positioned therebetween to form the valve assembly.

11. The apparatus of claim 8, wherein the mouth opening is circular and the valve assembly defines an annular ring for surrounding the mouth opening with the passageway extending therethrough.

12. The apparatus of claim 8, wherein fastening devices connect the valve assembly to the facemask body.

13. A system for protecting the respiratory system of a wearer from infectious agents that are transmitted through airborne droplets, the system comprising:

a protective facemask having a body for covering at least a portion of a face of the wearer, wherein the body has an inner surface adjacent to the face and an outer surface on an opposite side thereof, wherein the body of the facemask has a mouth opening directly in front of a mouth of the wearer, a valve assembly comprising;

a mounting plate frictionally engaging the protective facemask body inner surface, surrounding the mouth opening, at least partially, and defining a first opening that is co-extensive with the mouth opening, at least partially, a retaining plate frictionally engaging and directly contacting the protective facemask body outer surface, surrounding the mouth opening, at least partially, and defining a second opening that is co-extensive with the mouth opening, at least partially, a tubular spacer positioned between the mounting plate and the retaining plate inserted into the mouth opening to define a passageway connecting the first opening to the second opening for nourishment to flow therethrough, wherein the tubular spacer is unitary with the mounting plate, a gasket for sealing the passageway, wherein the gasket is frictionally engaged by and directly contacting the mounting plate and the retaining plate, and a removeable cap for covering the retaining plate, wherein the removable cap is unitary with the retaining plate, wherein the mounting plate and the retaining plate define jaws for gripping the protective facemask body to hold the valve assembly in place, wherein the valve assembly has a bore extending through the mounting plate, the retaining plate, and the spacer to define a passageway for passing a nourishment delivery device into the facemask through the valve assembly so that the nourishment delivery device enters the mouth of the wearer, and wherein the gasket surrounds the tubular nourishment delivery device, at least partially.

14. The system of claim 13, wherein the tubular nourishment delivery device is a device selected from the group consisting of a straw, a syringe, and a needle.

15. The system of claim 13, wherein the removeable cap is made from rigid molded plastic.

16. The system of claim 13, wherein the gasket includes a plurality of portions that deflect when the tubular nourishment delivery device extends therethrough.

17. The system of claim 13, wherein the retaining plate includes a notch therein, and wherein the removable cap includes a projection capable of being inserted into the notch to facilitate closing the of the removable cap.

18. The system of claim 13, wherein the gasket comprises a flat annular disk with a circular lip.

\* \* \* \* \*